(12) United States Patent
Teets et al.

(10) Patent No.: US 9,101,688 B2
(45) Date of Patent: *Aug. 11, 2015

(54) CONTAINMENT SYSTEM FOR DELIVERY OF BIOLOGICAL PRODUCTS AND METHOD OF SURGERY

(75) Inventors: J. Maxwell Teets, Cleveland Heights, OH (US); Christopher Bare, Naples, FL (US); Tara L. Schaneville, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 1562 days.

This patent is subject to a terminal disclaimer.

(21) Appl. No.: 12/198,846

(22) Filed: Aug. 26, 2008

(65) Prior Publication Data

US 2009/0060975 A1 Mar. 5, 2009

Related U.S. Application Data

(60) Provisional application No. 60/968,256, filed on Aug. 27, 2007.

(51) Int. Cl.
| | | |
|---|---|---|
| *A61F 2/00* | (2006.01) | |
| *A61K 9/48* | (2006.01) | |
| *A61K 35/16* | (2006.01) | |
| *A61K 35/28* | (2006.01) | |
| *A61L 27/24* | (2006.01) | |
| *A61K 35/14* | (2015.01) | |
| *A61K 35/19* | (2015.01) | |
| *A61L 27/36* | (2006.01) | |

(52) U.S. Cl.
CPC .............. *A61L 27/24* (2013.01); *A61K 9/4866* (2013.01); *A61K 35/14* (2013.01); *A61K 35/16* (2013.01); *A61K 35/19* (2013.01); *A61K 35/28* (2013.01); *A61L 27/3616* (2013.01); *A61L 27/3654* (2013.01)

(58) Field of Classification Search
CPC . C08L 89/06; A61L 27/3608; A61L 27/3654; A61L 27/24; A61L 2420/04; A61L 2420/08; A61L 24/102; A61L 27/3852; A61L 31/044; A61L 27/3616; A61K 9/4866; A61K 35/14; A61K 35/16; A61K 35/28; A61K 35/19
USPC ................. 424/423, 456, 529, 530, 549, 484; 514/778, 772.3, 772.2, 781, 777, 779
See application file for complete search history.

(56) References Cited

U.S. PATENT DOCUMENTS

| | | | |
|---|---|---|---|
| 2002/0006437 A1* | 1/2002 | Grooms et al. ............... | 424/451 |
| 2004/0146561 A1* | 7/2004 | Sakurai et al. ............... | 424/486 |
| 2005/0008629 A1* | 1/2005 | Arm ........................... | 424/93.71 |
| 2006/0030940 A1* | 2/2006 | Schmieding ............... | 623/13.14 |
| 2006/0159663 A1* | 7/2006 | Lu et al. ...................... | 424/93.7 |
| 2007/0077267 A1* | 4/2007 | Molz et al. ................... | 424/423 |
| 2007/0191849 A1* | 8/2007 | ElAttrache et al. ........... | 606/72 |
| 2008/0166421 A1* | 7/2008 | Buhr et al. ................... | 424/530 |
| 2008/0221527 A1* | 9/2008 | Bradley et al. ............... | 604/187 |

OTHER PUBLICATIONS

Umehara et al Surgery, 2001, 130, 513-520.*
Umehara et al Surgery 2001, 130, 513-520.*
D. Ranly, DDS, PhD et al., "Platelet-Rich Plasma Inhibits Demineralized Bone Matrix-Induced Bone Formation in Nude Mice", The Journal of Bone and Joint Surgery, Incorporated, www.ejbjs.org, Mar. 14, 2007, pp. 139-151.
Y. Umehara et al., "Improved Survival and Ammonia Metabolism by Intraperiotoneal Transplantation of Microencapsulated Hepatocytes in Totally Hepatectomized Rats," Surgery, vol. 130, No. 3, Sep. 1, 2001, pp. 513-520.

* cited by examiner

*Primary Examiner* — Anoop Singh
(74) *Attorney, Agent, or Firm* — Dickstein Shapiro LLP

(57) ABSTRACT

Methods and systems for delivering biological products to different surgical sites during surgery are described. The biological product is encapsulated or contained within a containment system comprising a carrier such as collagen carrier. The containment system may be formed of water soluble polymers that are natural, synthetic or semisynthetic, provided into films that may be made or molded into various shapes and sizes, and that may be manipulated to confer specific properties of such films. The water soluble films may be processed into capsules, packets or other containers.

5 Claims, 6 Drawing Sheets

CONTAINMENT SYSTEM FOR DELIVERY OF BIOLOGICAL PRODUCTS AND METHOD OF SURGERY

CROSS-REFERENCE TO RELATED APPLICATIONS

This application claims the benefit of U.S. Provisional Application No. 60/968,256, filed Aug. 27, 2007, the entire disclosure of which is incorporated by reference herein.

FIELD OF THE INVENTION

The present invention relates to the field of surgery and, more particularly, to containment systems for delivery of biological products such as blood or bone marrow aspirate (BMA) to arthroscopic sites during reconstructive surgeries.

BACKGROUND OF THE INVENTION

Tendon and ligament disruption at the joint has an unpredictable outcome and surgery is often needed to reconstruct and repair the injury. Adult stem cells such as Bone Marrow Stromal Cells (BMSCs) have been successfully isolated, although these stem cells lack definite specificity because there is no known exceptional phenotypic marker. These BMSCs are pluripotential stem cells that have been shown to have the potential to differentiate into bone, cartilage muscle, tendon, and fat cells, and can potentially aid in the healing process.

BRIEF SUMMARY OF THE INVENTION

The present invention provides methods and systems for delivering biological products such as autologous bodily fluids (for example, blood, platelet rich plasma (PRP) or autologous conditioned plasma (ACP)) or bone marrow aspirate (BMA) to different surgical sites during surgery (for example, arthroscopic surgery). The biological product is contained or encapsulated within a containment system comprising a carrier such as collagen carrier. The containment system may be a capsule formed of water soluble polymers, either natural, synthetic or semisynthetic, provided into films that may be made or molded into various shapes and sizes, and that may be manipulated to confer specific properties (such as solubility or degradation rates according to a specific environment, for example) of such films. The water soluble films may be processed into capsules, packets or other containers.

Other features and advantages of the present invention will become apparent from the following description of the invention which refers to the accompanying drawings.

DETAILED DESCRIPTION OF THE INVENTION

Figure 1:
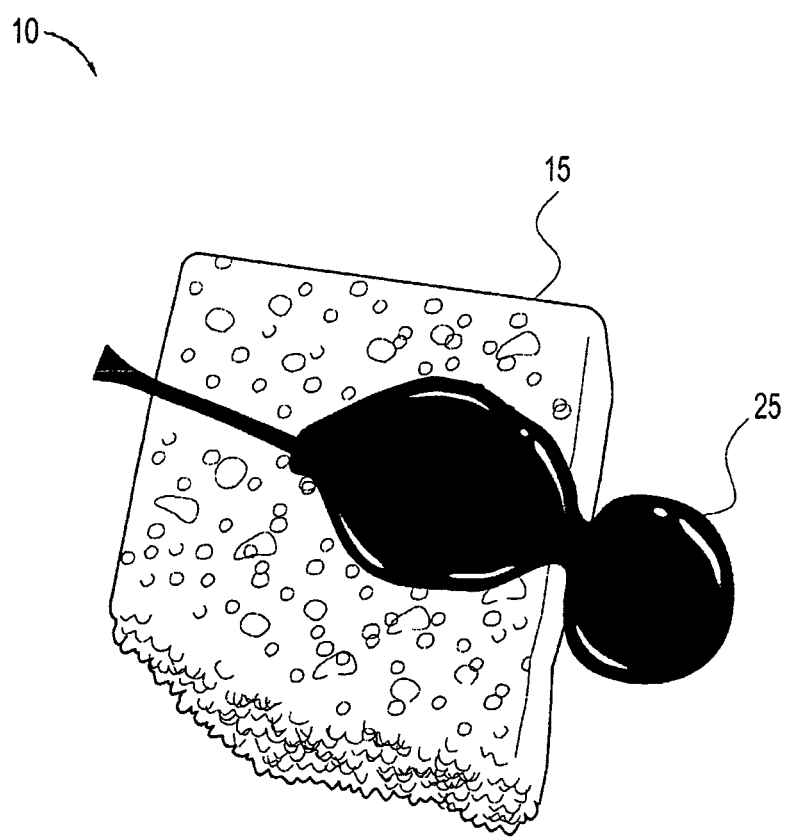
FIG. 1 illustrates sticky fibrillar collagen with blood.

The examples provided below detail the preferred embodiments of the present invention. Other features, embodiments, and advantages of the invention beyond those discussed in the detailed description will be obvious to those skilled in the art. Those skilled in the art should appreciate that many changes may be made to the present invention without departing from the scope or spirit of the present invention.

The present invention provides methods and systems for delivering biological products such as BMA and autologous bodily fluids (for example, blood, platelet rich plasma (PRP) or autologous conditioned plasma (ACP)) to different surgical sites (for example, the distal femur during ACL surgery or the proximal humeral head during rotator cuff repair) during arthroscopic surgery. The biological product is contained or encapsulated within a containment system comprising a carrier such as collagen carrier. The containment system may be a capsule formed of water soluble polymers, either natural, synthetic or semisynthetic, provided into films that may be made or molded into various shapes and sizes. The water soluble films may be also manipulated to confer specific properties (such as solubility or degradation rates according to a specific environment, for example) of such films. The water soluble films may be processed into capsules, packets or other containers.

The present invention also provides a method of delivering blood, BMA, PRP and/or ACP to a surgical site (for example, damaged tissue at an arthroscopic resurfaced site). The method comprises the steps of: (i) providing blood, BMA, PRP and/or ACP contained in a delivery system comprising a carrier (for example, a collagen sponge); and (ii) securing the blood, BMA, PRP and/or ACP encapsulated in the capsule at the defect site (arthroscopic resurfaced site).

In an exemplary embodiment, the present invention provides a method of delivering BMA to a surgical site (for example, damaged tissue at an arthroscopic resurfaced site). The method comprises the steps of: (i) providing BMA encapsulated in a capsule comprising a BMA carrier (for example, a collagen sponge); and (ii) securing the BMA encapsulated in the capsule at the defect site (arthroscopic resurfaced site).

According to a preferred embodiment of the present invention, water soluble films may be used for the capsule material. Water soluble films are used within a wide range of applications for multiple industries including packaging, textile, and healthcare industries. These films can be made into several sizes and molded into multiple shapes. These products are ideal for powders, liquids and granules that require protection to maintain their integrity prior to usage. The films may be designed to meet product requirements and enhance product performance through new formulations and technologies.

These films are developed to have a range of solubility characteristics. The dissolution rate is dependent on, but not limited to, the type of polymer base material chosen, molecular weight of the material, density of the film, thickness of film, the use of additives, use of coatings, and the degradation environment. Each polymer base film may be optimized to have desired solubility characteristics. Also, the range of thicknesses for water-soluble films is very broad and variable. Higher molecular weight polymer materials, denser and thicker films may have slower degradation rates. Additives may be added to the polymers or coatings added to the films to perform specific functions, i.e., to delay or speed up dissolution rate, affect stretch, and assist in primary and secondary processes of the film. In addition, the temperature and the amount of fluid in the environment may affect the degradation rate.

Non-limiting examples of base solutions used to make the films in accordance with embodiments of the present invention include the following: polyvinyl alcohol (PVOH), pectin, hydroxypropylmethyl cellulose (HPMC), carboxymethylcellulose (CMC), pullulan, carrageenan, xanthan gum, alginate, and other starch or polymer systems, among many others.

The above-described exemplary materials have been used to make water soluble films for food and/or pharmaceutical applications. These materials are used as temporary implant scaffolds for delivering blood, BMA, PRP and/or ACP according to embodiments of the present invention.

In an exemplary embodiment only, delivery system 100 of the present invention comprises blood impregnated collagen 10 that is contained (encapsulated) within capsule 50. Delivery system 100 may comprise, in lieu of the blood, BMA or other blood fractions and/or blood components, for impregnating the collagen matrix.

In another exemplary embodiment only, delivery system 100 of the present invention comprises a composition including bone marrow stromal cells (BMSCs) or mesenchymal cells isolated from bone marrow aspirate, the composition having osteogenic and/or osteoinductive cell proliferative activity. The BMSCs or the mesenchymal cells may be isolated at the time of surgery (intraoperatively) and they may be collected from various sites such as iliac crest, proximal humeral head or distal femur. The composition may be optionally employed or combined with a bone-compatible matrix to facilitate slow release of the cells at the treatment site (i.e., at the arthroscopic site) and/or provide a structure for developing bone. The composition (including bone marrow stromal cells (BMSCs) or mesenchymal cells) is contained or encapsulated within the containment system (such as capsule 50) comprising a carrier such as collagen carrier.

Additional components such as autologous conditioned plasma (ACP), platelet-rich plasma (PRP), growth factors, additional antiseptic chemicals and/or antibiotics and/or electrolytes, or hormones or site-specific hybrid proteins (that promote or enhance the wound healing effectiveness of the growth factors) may be additionally or alternatively provided as part of the delivery system 100 of the present invention.

Growth factors may comprise proteinaceous factors, for example, which play a role in the induction or conduction of growth of tissue, ligaments, bone, cartilage or other tissues associated with bone or joints.

The delivery system 100 of the present invention is designed to be inserted at a repair site and to further adhere to the resurfaced tissue (bone, ligament or cartilage). The delivery system 100 of the present invention may be placed over a prepared osteochondral socket or tunnel, and/or may be used in conjunction with various osteochondral cores, for example.

The materials and methods described below address the performance of an exemplary gelatin capsule in a fluid environment:

Materials/Methods

A 50 ml plexiglass cube was used to simulate the "joint space" and a screen was placed over the outlet to keep the capsule inside. Room temperature water was pumped through the cube with an Arthrex pump at a flow rate of about 500 ml/min to create a worst case scenario. The typical flow using the arthroscopic pump may be about 100-300 ml/min.

About half of a "sticky" fibrillar collagen matrix 15 (from Kensey Nash, for example) was impregnated/saturated with about 0.5 ml of bovine blood 25 (FIG. 1) to obtain the blood impregnated collagen 10 of FIG. 1. The whole patch may be hydrated with about 1 ml of fluid and then molded into a new shape. Subsequent to the impregnation of collagen with blood, two groups were tested: (i) encapsulated collagen with blood (FIG. 2) and (ii) non-encapsulated collagen with blood (i.e., collagen with blood only).

Figure 2:
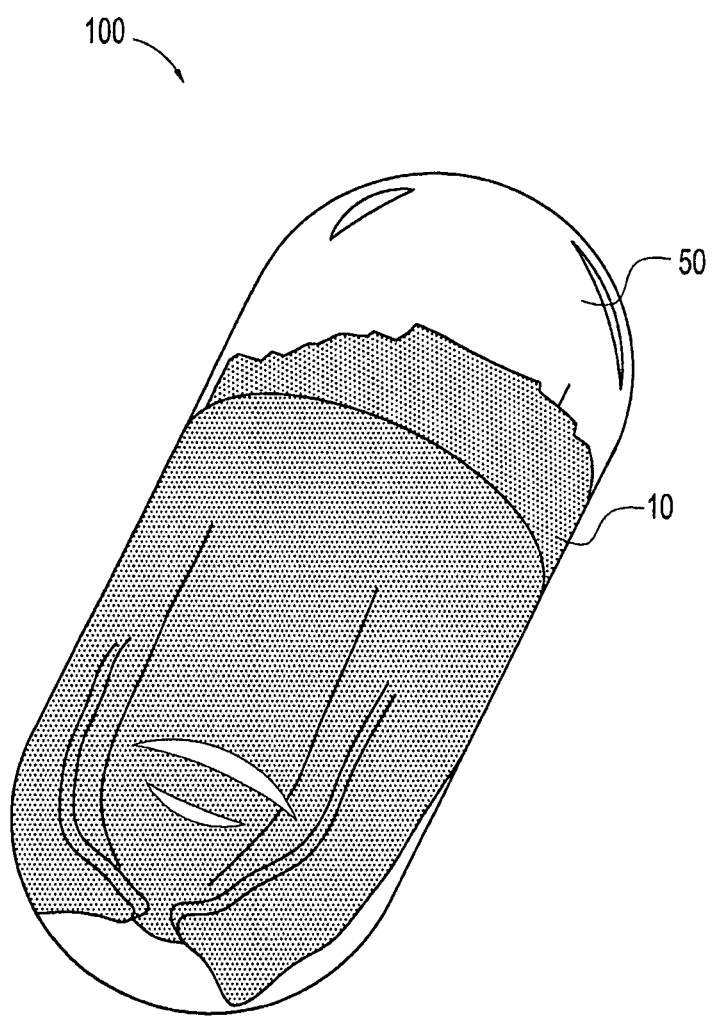
FIG. 2 illustrates fibrillar collagen encapsulated in a gelatin capsule and in accordance with an embodiment of the present invention.

FIG. 2 illustrates the blood impregnated collagen 10 of FIG. 1 which is encapsulated in capsule 50 to form delivery system 100 (which is placed inside the cube). In an exemplary embodiment, capsule 50 of delivery system 100 is a size 00 gelatin capsule.

Each group was exposed to fluid in the cube for at least 10 minutes.

Results

Figure 3:
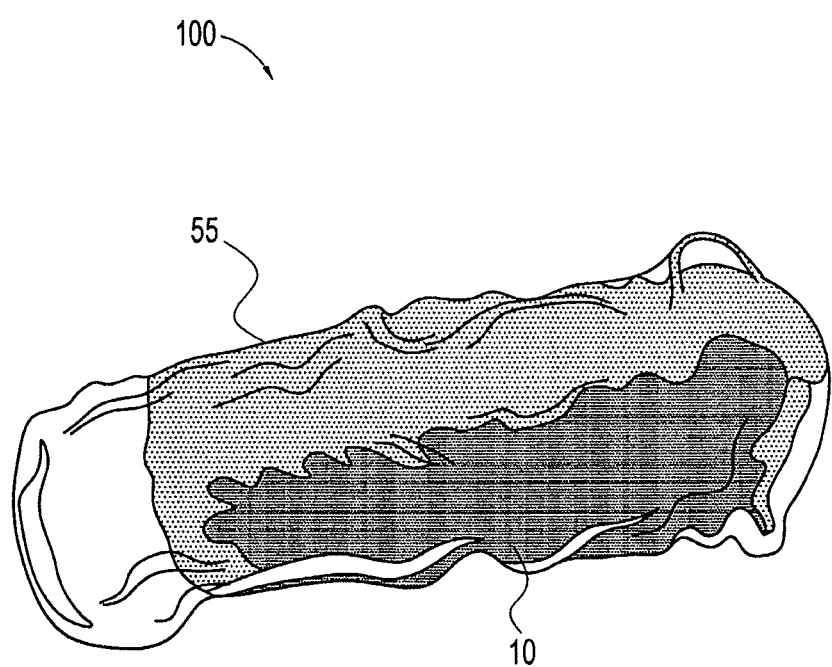
FIG. 3 illustrates the encapsulated fibrillar collagen of FIG. 2 after testing.

The gelatin capsule 50 remained integral for the duration of the testing which helped maintain the maximum volume of blood inside the collagen matrix. The gelatin capsule 50 lost its initial rigid shape (FIG. 3) and became about flat in a fluid environment (i.e., capsule 50 of FIG. 2 changed its first shape to a second shape of capsule 55 of FIG. 3). Small portions of the capsule broke and dissolved, but overall capsule 55 maintained a coating around the collagen carrier (FIG. 3).

The collagen matrix without a capsule did retain some of the blood throughout the 10 minutes, but some blood was also washed out exposing white collagen fibers. Also, under flow, the non-encapsulated collagen became a wispy mass of collagen fibers that began to break apart.

Figure 4:
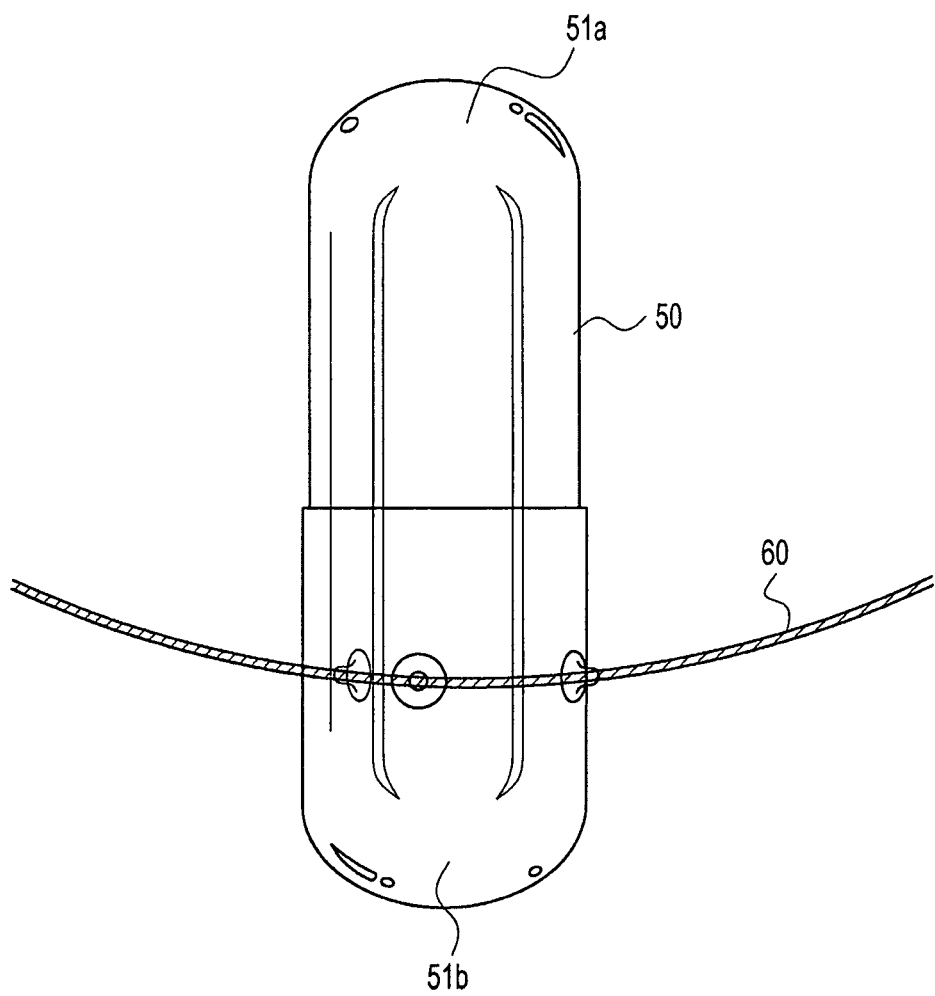
FIG. 4 illustrates a 3-0 suture through the capsule of FIG. 2.

A suture 60 (for example, a size 3-0 suture 60) is passed through capsule 50 and placed in a fluid environment, as shown in FIG. 4. According to exemplary embodiments of the present invention, the capsule is sutured (with suture 60, for example) and, to maximize stability, the capsule is preferably sutured through the portion of the capsule where each half overlaps (i.e., at about the center portion of capsule 50). In a fluid environment, the rounded ends 51a, 51b (FIG. 4) of the capsule 50 are the first to dissolve.

Figure 5A:
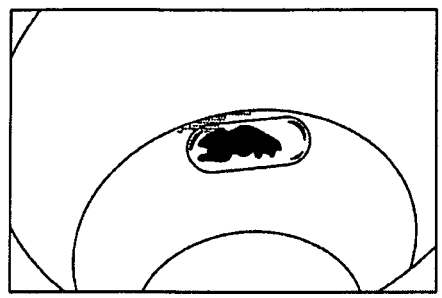
FIGS. 5A-I illustrate a gel capsule in water at various time intervals (between 0 min to 75 min).
Figure 5B:
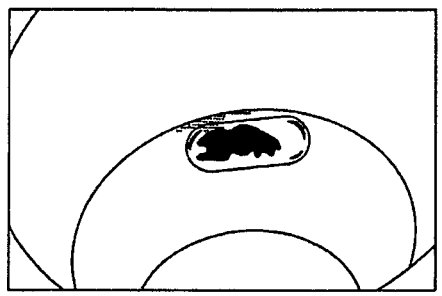
Figure 5C:
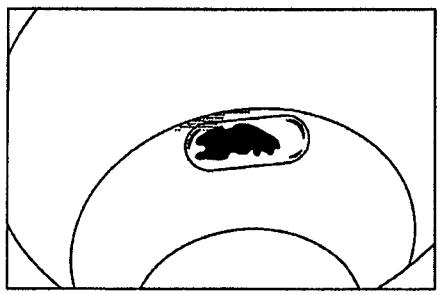
Figure 5D:
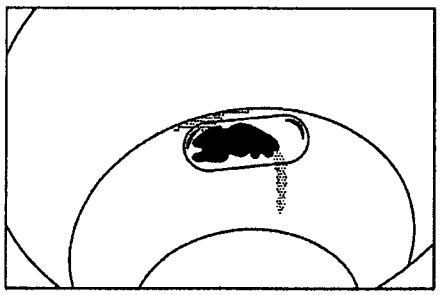
Figure 5E:
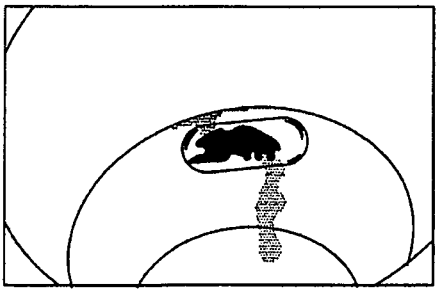
Figure 5F:
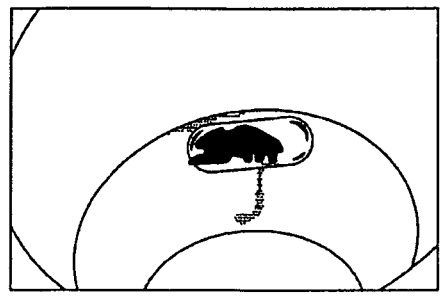
Figure 5G:
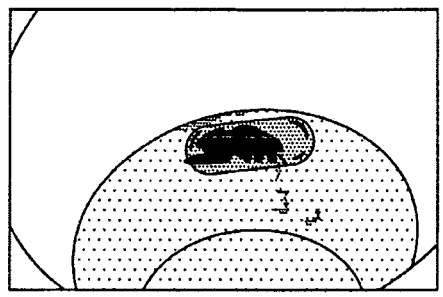
Figure 5H:
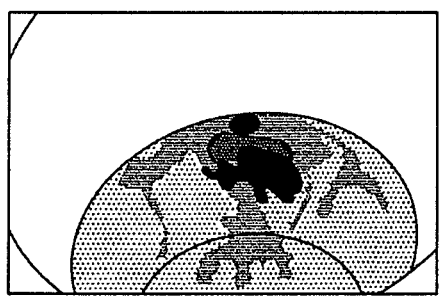
Figure 5I:
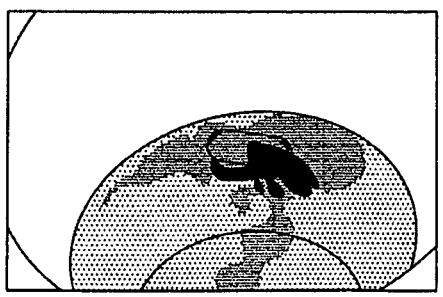

Temperature affects dissolution rate. The gel capsule dissolves faster at a higher temperature. The results of a pilot dissolution study with release of methylene blue dye in a capsule maintained at stable temperature (for example, at about 37° C.) are exemplified in FIGS. 5A-I. FIGS. 5A-C illustrate gel capsule 50 in water at constant 37° C. (methylene blue about 1%) at t=0 min (FIG. 5A); t=1.5 min (FIG. 5B); and t=4.5 min (FIG. 5C). FIGS. 5D-I illustrate the capsule starting to bleed methylene blue dye at t=9.0 min (FIG. 5D); t=15 min (FIG. 5E); t=20 min (FIG. 5F); t=31 min (FIG. 5G); t=60 min (FIG. 5H); and t=75 min (FIG. 5I). The results of the pilot dissolution study demonstrate that the encapsulated collagen matrix (carrier) of the present invention retained blood for more than about 1 hour. In this manner, a maximum volume of blood (for example, BMA) is maintained within the collagen matrix.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of delivering biological products to an arthroscopic site, comprising the steps of:
   conducting arthroscopic surgery at an arthroscopic site to obtain a resurfaced arthroscopic site;
   providing a water soluble gelatin capsule and a collagen matrix impregnated with a biological product;

encapsulating or containing the collagen matrix impregnated with the biological product within the water-soluble capsule;

securing the water soluble capsule with the encapsulated collagen matrix impregnated with the biological product at the resurfaced arthroscopic site during the arthroscopic surgery; and wherein said water soluble gelatin capsule dissolves over time to release the biological product impregnated in the collagen matrix and to thereby deliver the biological product at damaged tissue at the resurfaced arthroscopic site, wherein the resurfaced arthroscopic site is damaged cartilage, and wherein the biological product is selected from the group consisting of autologous conditioned plasma and autologous bone marrow aspirate.

2. The method of claim 1, wherein the biological product is autologous conditioned plasma, and wherein the autologous conditioned plasma is obtained by subjecting blood to at least one centrifugation step to obtain the autologous conditioned plasma.

3. The method of claim 1, wherein the biological product is autologous bone marrow aspirate.

4. A method of treating tissue in a mammal, comprising:

providing autologous conditioned plasma from a residual blood component of a mammal;

providing a hydrated collagen support with the autologous conditioned plasma to obtain a hydrated collagen support;

encapsulating or containing the hydrated collagen support within a gelatin capsule to obtain a gelatin containment system with the hydrated collagen support;

conducting Anterior cruciate ligament (ACL) surgery in the mammal in need thereof; and securing and delivering the gelatin containment system into distal femur, or to the distal femur during the ACL surgery, to promote tissue growth, wherein the gelatin containment system retains its initial shape for about 10 minutes when immersed in water, saline solution or body fluid, at about 37° C.

5. The method of claim 4, further comprising the step of adding, to the hydrated collagen support, a component selected from the group consisting of growth factors, antiseptics, antibiotics and electrolytes.

\* \* \* \* \*